United States Patent
Chen et al.

(10) Patent No.: US 11,786,215 B2
(45) Date of Patent: Oct. 17, 2023

(54) METHODS OF DETECTING, MEASURING, OR IMAGING A CONCENTRATION OR LOCATION OF A THERAPEUTIC AGENT

(71) Applicants: Hong Chen, St. Louis, MO (US); Yaoheng Yang, St. Louis, MO (US); Jeffrey Williamson, St. Louis, MO (US)

(72) Inventors: Hong Chen, St. Louis, MO (US); Yaoheng Yang, St. Louis, MO (US); Jeffrey Williamson, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/751,197

(22) Filed: Jan. 23, 2020

(65) Prior Publication Data

US 2020/0229793 A1    Jul. 23, 2020

Related U.S. Application Data

(60) Provisional application No. 62/795,801, filed on Jan. 23, 2019.

(51) Int. Cl.
*A61B 8/08* (2006.01)
*A61N 7/02* (2006.01)
*A61N 7/00* (2006.01)

(52) U.S. Cl.
CPC ............ *A61B 8/481* (2013.01); *A61B 8/0808* (2013.01); *A61B 8/5207* (2013.01); *A61N 7/02* (2013.01); *A61N 2007/0039* (2013.01)

(58) Field of Classification Search
CPC ............ A61B 2090/378; A61B 8/0808; A61B 8/4416; A61B 8/481; A61B 8/5207; A61B 8/5223; A61N 2007/0039; A61N 7/02
See application file for complete search history.

(56) References Cited

U.S. PATENT DOCUMENTS

| 2011/0125080 A1* | 5/2011 | Shi | A61K 9/0009 604/20 |
| 2017/0043149 A1* | 2/2017 | Liu | A61B 5/4064 |
| 2019/0009108 A1* | 1/2019 | Lee | A61B 8/481 |

OTHER PUBLICATIONS

Kim, H. et al. PET/CT imaging evidence of FUS-mediated (18) F-FDG uptake changes in rat brain. Med. Phys. 40, 33501 (2013) (Year: 2013).*

(Continued)

*Primary Examiner* — Yi-Shan Yang
*Assistant Examiner* — Alexei Bykhovski (57) ABSTRACT

Systems and methods for monitoring and controlling delivery of a therapeutic compound to a brain of a subject using FUS-BBBD are disclosed. The method includes treating the brain of the subject with focused ultrasound in combination with microbubbles for blood-brain barrier disruption (FUS-BBBD), administering the therapeutic agent to the subject; and obtaining a map of a concentration of the therapeutic agent delivered to the brain of the subject using passive cavitation imaging (PCI). The delivery of focused sound may be modulated to match the map of the concentration of the therapeutic agent delivered to the brain of the subject to a desired spatial distribution of the therapeutic agent.

12 Claims, 10 Drawing Sheets
(10 of 10 Drawing Sheet(s) Filed in Color)

(56) References Cited

OTHER PUBLICATIONS

Salgaonkar et al, Passive cavitation imaging with ultrasound arrays, J. Acoust. Soc. Am. 126, Dec. 6, 2009, 3071-3083 (Year: 2009).*
Arvanitis CD, Livingstone MS, McDannold N (2013) Combined ultrasound and MR imaging to guide focused ultrasound therapies in the brain. Phys Med Biol 58: 4749-4761. (Year: 2013).*
Sun, T. et al. Closed-loop control of targeted ultrasound drug delivery across the bloodbrain/tumor barriers in a rat glioma model. Proc. Natl. Acad. Sci. 114, EI 0281-EI 0290 (2017). (Year: 2017).*
Wu S.-Y. et al. (2018) Efficient blood-brain barrier opening in primates with neuronavigation-guided ultrasound and real-time acoustic mapping. Sci. Rep. vol. 8, p. 7978.
Arvanitis, C. D., Livingstone, M. S., Vykhodtseva, N. & McDannold, N. Controlled ultrasound-induced blood-brain barrier disruption using passive acoustic emissions monitoring. *PLoS One* 7, e45783 (2012).
O'Reilly, M. A. & Hynynen, K. Feedback-controlled focused ultrasound disruption by using an acoustic emissions-based controller. *Radiology* 263, 96-106 (2012).
Sun, T. et al. Closed-loop control of targeted ultrasound drug delivery across the blood-brain/tumor barriers in a rat glioma model. *Proc. Natl. Acad. Sci.* 114, E10281-E10290 (2017).

* cited by examiner

METHODS OF DETECTING, MEASURING, OR IMAGING A CONCENTRATION OR LOCATION OF A THERAPEUTIC AGENT

CROSS-REFERENCE TO RELATED APPLICATIONS

This application claims the benefit of U.S. Provisional Application No. 62/795,801 filed Jan. 23, 2019, the contents of which are incorporated by reference in its entirety.

STATEMENT REGARDING FEDERALLY SPONSORED RESEARCH OR DEVELOPMENT

This invention was made with government support under MH116981 awarded by the National Institutes of Health. The government has certain rights in the invention.

FIELD OF THE DISCLOSURE

The present disclosure generally relates to precision medicine and personalized brain disease treatment.

BACKGROUND OF THE DISCLOSURE

Focused ultrasound in combination with microbubbles for blood-brain barrier disruption (FUS-BBBD) has been established as a promising technique for the delivery of therapeutic agents to a targeted brain location without invasive surgery. The blood-brain barrier (BBB) excludes ~100% of large-molecule drugs and 98% of small-molecule drugs from entering the brain parenchyma. FUS-BBBD utilizes the mechanical interactions between microbubbles and the surrounding blood vessels to enhance the BBB permeability, allowing various therapeutic agents in the systemic circulation to be delivered across the BBB to the brain tissue. Extensive preclinical studies have been performed to develop the FUS-BBBD technique, including evaluation of its feasibility and safety in smaller animal models (e.g., mice, rats and rabbits) and larger animal models (e.g., pigs and non-human primates); optimization of treatment protocols; assessment of therapeutic efficacy for various diseases; and revealing its fundamental mechanisms. Recently, a clinical trial successfully demonstrated the feasibility and safety of FUS-BBBD in patients with Alzheimer's disease. Despite these great advancements of the FUS-BBBD technique, there is an unmet need for a treatment monitoring technique that is capable of predicting the location and concentration of therapeutic agents delivered by FUS-BBBD. This capability is critically needed to verify localized drug delivery to the targeted brain location without off-target effects in the brain; assess whether the concentrations of the delivered agents reach the desired therapeutic levels; characterize variations among repeated treatments; and develop real-time feedback control of the FUS parameters to deliver the desired concentrations of drugs to the targeted locations.

Several existing imaging techniques have been used for the assessment of FUS-BBBD treatment outcome. Magnetic resonance imaging (MRI) is the most commonly used imaging modality for the assessment of FUS-mediated BBB permeability changes based on the leakage of MR contrast agents from the blood into the brain parenchyma. Positron emission tomography (PET) and single photon emission computed tomography (SPECT) in combination with radio-labeled therapeutic agents provide noninvasive, sensitive, and quantitative methods for directly assessing the spatial distribution of radiolabeled agents. Several studies have used PET or SPECT to evaluate the spatial distributions of radiolabeled agents in the brain after FUS-BBBD treatment. Our previous study verified that in vivo PET imaging can reliably estimate the concentrations of the $^{64}$Cu-labeled gold nanoclusters ($^{64}$Cu—AuNCs) delivered to the brain using ex vivo gamma counting and inductively coupled plasma mass spectrometry (ICP-71 MS). The $^{64}$Cu radioactivity was found to be linearly correlated with the Au concentration quantified using ICP-MS($R^2$=0.94), which confirmed the radiolabel stability of $^{64}$Cu for accurate measurement of $^{64}$Cu—AuNCs distribution. However, MRI, PET, and SPECT cannot be used to perform intraprocedural monitoring of the FUS treatment.

Among existing techniques, passive cavitation monitoring, including passive cavitation detection (PCD) and passive cavitation imaging (PCI), is the most commonly used technology for FUS-BBBD treatment monitoring. The underlying concept is that mechanical oscillations of the microbubbles emit ultrasound waves that can be detected using ultrasound sensors to passively "listen" to the secondary acoustic emissions by the microbubbles (this differs from active pulse-echo ultrasound imaging). Passive cavitation detection (PCD), using a single-element ultrasound sensor, has been broadly used for real-time FUS-BBBD treatment monitoring to quantify cavitation levels, differentiate between cavitation modes (i.e., stable cavitation and inertial cavitation), investigate bioeffects of cavitation, and develop feedback control algorithms to enhance the FUS treatment safety and efficacy. Stable cavitation (SC, small amplitude microbubble oscillation) can be characterized by the detection of harmonic emissions in the frequency domain, while inertial cavitation (IC, large amplitude microbubble oscillation followed by violent collapse) can be characterized by broadband emissions. PCD has been implemented for real-time monitoring of the FUS-BBBD treatment and controlling FUS exposure parameters using a closed-loop control algorithm. Although PCD has been shown to be a useful tool for FUS-BBBD monitoring, it cannot detect the spatial distribution of cavitation. PCI, integrating multi-element sensor arrays with beam-forming techniques, can be used to image the spatial distribution of cavitation. Using available ultrasound imaging probes, different 2D PCI algorithms have been introduced, for example, time-domain delay-and-sum beamformer, time-domain robust Capon beamformer, frequency domain delay-and-sum beamformer, robust beamforming by linear programming, and the angular spectrum method. Moreover, a recent study demonstrated the feasibility of 3D passive cavitation imaging using a customized 2D array. However, to our knowledge, only two studies have been published on evaluating the feasibility of using PCI to predict the location of BBBD by correlating PCI with the BBB permeability changes evaluated by post-treatment contrast-enhanced MRI. No study has been reported on using PCI to estimate the spatial distribution (both location and concentration) of therapeutic agents delivered by FUS-BBBD.

Other objects and features will be in part apparent and in part pointed out hereinafter.

SUMMARY OF THE INVENTION

Among the various aspects of the present disclosure is the provision of methods for modulating drug delivery to a subject and methods for detecting, imaging, or measuring a concentration and/or location of the therapeutic agent delivered by FUS-BBBD using passive cavitation imaging (PCI).

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure. Those of skill in the art will understand that the drawings, described below, are for illustrative purposes only. The drawings are not intended to limit the scope of the present teachings in any way.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

The present disclosure is based, at least in part, on the discovery of a novel technique for precision medicine and personalized brain disease treatment. As shown herein, the present disclosure provides for a technique that combines focused ultrasound-induced blood-brain barrier disruption (FUS-BBBD) with passive cavitation imaging (PCI) for noninvasive, localized, and modulated brain drug delivery. FUS-BBBD is a promising technique for noninvasive and localized brain drug delivery. Passive cavitation imaging (PCI) is an ultrasound imaging technique that is capable of predicting the location and concentration of nanoclusters delivered by FUS-BBBD. As demonstrated in the examples provided below, PCI predicts the location and concentration of drugs delivered to the brain, after administering the drug using the FUS-BBBD method.

In various aspects, PCI monitoring of cavitation activity during FUS-BBBD administration of an active compound is used to obtain a map of stable cavitation dose (SCD) that is correlated with delivered drug concentration. In various other aspects, the PCI-based SCD map is transformed into a spatial map of delivered drug concentration based on a predetermined correlation between delivered drug concentration and SCD values. In various additional aspects, the transformed SCD map effectively "paints" a spatial distribution of delivered drug concentration, referred to herein as cavitation dose painting. In some aspects, this PCI-based cavitation dose painting technique in combination with FUS-BBBD is used to facilitate spatially targeted and modulated brain drug delivery.

Described herein is a technique that combines focused ultrasound-induced blood-brain barrier disruption (FUS-BBBD) with passive cavitation imaging (PCI) for noninvasive, localized, and modulated brain drug delivery. FUS-BBBD is a promising technique for noninvasive and localized brain drug delivery. Passive cavitation imaging (PCI) is an ultrasound imaging technique that is capable of predicting the location and concentration of nanoclusters delivered by FUS-BBBD by obtaining measurements of cavitation activity including, but not limited to stable cavitation dose (SCD), that is correlated with drug delivery concentration. As described herein, the PCI-measured cavitation activity, combined with the correlations of cavitation activity with drug delivery concentrations, predict the drug delivery location and concentration in the brain.

As described in the examples below, the potential of PCI for estimating the location and concentration of therapeutic agents delivered by FUS-BBBD was evaluated using radiolabeled gold nanoclusters ($^{64}$Cu—AuNCs). In vivo PET imaging was used to quantify the spatial distribution of $^{64}$Cu—AuNCs in the brain after FUS-BBBD treatment, and the spatial distribution of $^{64}$Cu—AuNCs was correlated with the cavitation activity detected by PCI during FUS-BBBD treatment. Transformation of PCI-detected cavitation activity using the correlations as described herein was demonstrated to provide a pixel-wise estimation of the delivered $^{64}$Cu—AuNCs concentration, a technique referred to herein as cavitation dose painting.

In various aspects, the PCI-based cavitation dose painting technique described herein is used to guide conformal delivery of therapeutic agents to targeted brain region using FUS-BBBD, thereby avoiding side effects in non-targeted brain areas. In some aspects, the PCI-based cavitation dose painting technique may facilitate control of distribution and dosing of cavitation to deliver higher concentrations of therapeutic agents to high-risk target subvolumes while treating lower-risk subvolumes by delivering lower concentrations of therapeutic agents. The PCI-based cavitation dose painting technique disclosed herein facilitates controlled and precise brain drug delivery.

Without being limited to any particular theory, the spatial resolution of PCI is determined by the diffraction pattern of the imaging array with a lateral resolution at the scale of 10× of the axial resolution, which limits the accuracy of PCI in predicting the agent delivery location in the axial direction. As described in the examples below, the capability of PCI to measure the location of FUS-BBBD mediated drug delivery was evaluated by quantifying the offsets between the pixel location of the maximum stable cavitation dose ($SCD_{max}$) obtained using PCI as compared to the pixel location with the highest concentration of $^{64}$Cu—AuNCs obtained using PET/CT imaging. As described in the examples below, offsets of 0.3±0.4 mm in the transverse direction and 1.6±1.1 mm in the axial direction were obtained, which were comparable to offsets obtained using contrast-enhanced MRI to infer the locations of the delivered agents. However, the physicochemical properties of the MR contrast agents used in the previous studies were different from the therapeutic agents to be delivered by FUS-BBBD, and thus the biodistribution of the MR contrast agents may not accurately represent the distribution of the delivered therapeutic agent. Because the spatial resolution of PCI as evaluated herein directly imaged the distribution of $^{64}$Cu—AuNCs with physicochemical properties representative of the therapeutic agents to be delivered by FUS-BBBD, the PCI-based cavitation dose painting technique disclosed herein provides a noninvasive, highly sensitive, and quantitative method for assessing the efficiency of nanoparticle delivery and their spatial distribution. In various aspects, other therapeutic agents beside nanoparticles may be similarly radiolabeled to evaluate the agent's spatial distribution in the brain using PET.

Any known therapeutic agent suitable for administration to regions of the brain using FUS-BBBD may be administered with the PCI-based cavitation dose painting technique without limitation. Non-limiting examples of therapeutic agents compatible with the PCI-based cavitation dose painting technique include nanostructures such as nanoparticles, nanoshells, nanorods, and nanoclusters, chemotherapy drugs, peptides, and proteins.

In various aspects, the PCI-based cavitation dose painting technique makes use of a linear correlation between SCD quantified using PCI (2D) and the concentration of the delivered therapeutic agent. In one aspect, the linear correlation is determined by the analysis of a stable cavitation dose (SCD) distribution obtained using PCI as described herein and a corresponding concentration of delivered therapeutic agent including, but not limited to, $^{64}$Cu—AuNC at a pixel-by-pixel level, as described in detail in the examples below.

As discussed in the examples below, PCI-derived stable cavitation dose maps and PET-derived delivered $^{64}$Cu—AuNCs concentration maps varied between individual subjects treated using the same protocol, including FUS parameters (see FIGS. 4A, 4B, and 4C). Without being limited to any particular theory, previously reported variation among repeated FUS-BBBD treatments has been attributed to parameters related to inter-subject variation that are challenging to control, such as size distribution of microbubbles that reach as targeted brain location, circulating microbubble concentration in blood, blood vessel density within the treated region of the brain, and heterogeneous acoustic property of skull. In various aspects, the cavitation dose painting technique provides for treatment monitoring of individual subjects, reducing the effects of individual variation on the accuracy of the treatment monitoring.

In various aspects, PCI can be used to verify localized drug delivery to the targeted brain site without off-target effects in the brain, to assess whether the concentration of the delivered agent reaches a desired therapeutic level, and/or to characterize variations among repeated treatments. In some aspects, real-time PCI is used to quantify the cavitation dose during the course of FUS-BBBD treatment and to provide feedback control of the FUS parameters during the FUS-BBBD treatment. This PCI-feedback-controlled FUS-BBBD technique provides for controlling drug delivery location and spatially tailoring the delivered drug concentration to match the needed drug delivery doses at different subvolumes of the diseased brain region.

In various aspects, the cavitation dose painting technique is not limited to the delivery of nanoparticles, as described herein. In various other aspects, additional therapeutic agents including, but not limited to chemotherapeutic drugs, peptides, and proteins, are radiolabeled and injected to the patient at low doses (lower than the therapeutic level) after FUS-BBBD treatment to determine the correlation between PCI-derived SCD and PET-derived delivered drug concentrations as described herein to develop the cavitation dose painting technique for estimating and controlling the delivery of the additional therapeutic agent without radiolabeling.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program is provided, and the program is embodied on a computer readable medium. In one aspect, the system is executed on a single computer system, without requiring a connection to a sever computer. In a further aspect, the system is being run in a Windows® environment (Windows is a registered trademark of Microsoft Corporation, Redmond, Wash.). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes.

The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following examples illustrate various aspects of the disclosure.

Example 1: FUS-BBBD Treatment

To validate the use of focused ultrasound in combination with microbubbles for blood-brain barrier disruption (FUS-BBBD) as a method for the treatment of mouse brains, the following experiments were conducted.

C57BL/6 female mice (6-8 weeks, 20-25 g body weight, n=18 in total) were obtained from a commercial supplier (Charles River Laboratory, Wilmington, Mass., USA). Following a previously published procedure, each animal was prepared for FUS sonication by removing the head and coupled to a water container using ultrasound gel.

Figure 1A:
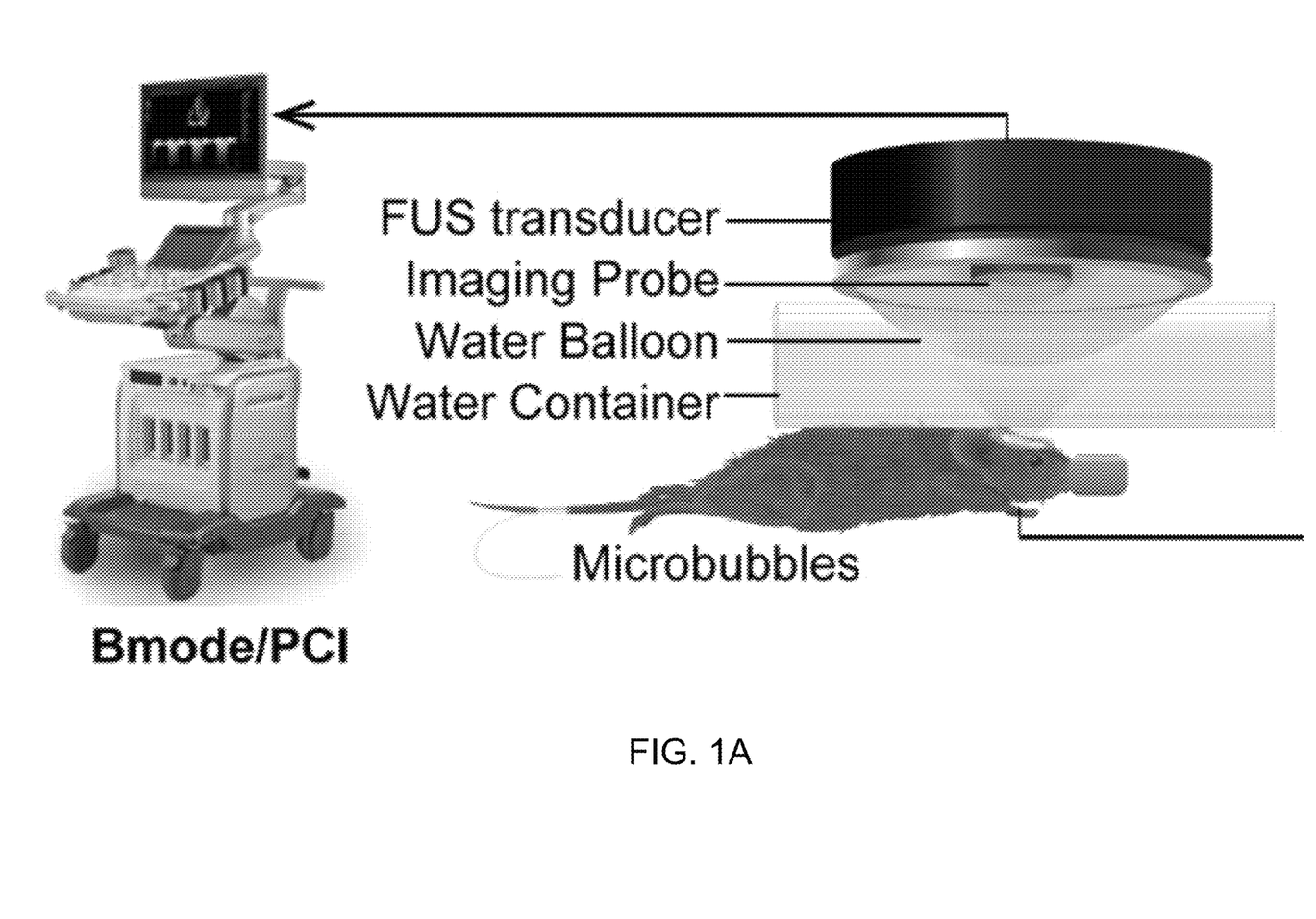
FIG. 1A is a schematic diagram illustrating a FUS-treatment system in accordance with one aspect of the disclosure.

The prepared mice were sonicated using a commercially available ultrasound image-guided focused ultrasound (FUS) system (VIFU 2000, Alpinion, Bothell, Wash., USA) that integrated a FUS component with a software programmable ultrasound imaging component as illustrated in FIG. 1A. The FUS component included a FUS transducer with a center frequency of 1.5 MHz, a focal depth of 60 mm, an aperture of 60 mm, and a circular central opening of 38 mm. The ultrasound imaging component included an ultrasound imaging probe consisting of a linear ultrasound transducer array with a bandwidth of 8-17 MHz and a center frequency of 12 MHz (L8-17, Alpinion, Seoul, Korea). The ultrasound imaging probe was positioned within the FUS transducer center opening to align the ultrasound imaging plane with the FUS focal plane.

The ultrasound imaging component was used for both treatment planning as described in the present example, and for passive cavitation imaging (PCI) as described in Ex. 2 below. The pressure amplitude and beam dimensions of the FUS transducer were calibrated using a needle hydrophone (HGL-0200, Onda, Calif., USA) in a degassed water tank prior to treatment of the mice. The pressures reported below were the measured hydrophone peak negative pressures corrected for 18% mouse skull attenuation. The full width at half maximum (FWHM) dimensions of the axial and lateral beams were 6.04 mm and 0.62 mm, respectively. Treatment planning was performed according to a previously published method using a metal grid to assist in aligning the FUS transducer focus at the left brainstem of each mouse.

Size-isolated microbubbles with a median diameter of 4-5 µm were prepared in-house according to a previously described protocol and diluted using sterile saline to a final concentration of about $8\times10^8$ number of microbubbles per ml. The diluted microbubble composition (volume=25 µL) were administered by a bolus injection via the tail veins of the mice. Immediately after injection (~9 s), the left brainstems of the mice were sonicated by the FUS system using the following parameters: center frequency=1.5 MHz, peak negative pressure=0.61 MPa, pulse length=6.7 ms, 266 pulse repetition frequency=5 Hz, and sonication duration=120 s.

After completion of sonication by the FUS system, the mice were administered radiolabeled gold nanoclusters ($^{64}$Cu—AuNCs) by intravenous injection (3.7 MBq/100 µci in 100 µL of saline). $^{64}$Cu—AuNCs were used as model agents based on any one or more of at least several characteristics including, but not limited to chemical stability, biocompatibility, ease of labeling via functionalization, and effectiveness as a theranostic nanomedicine. The $^{64}$Cu—AuNCs had a homogeneous size distribution with a hydrodynamic diameter of 5.60±0.50 nm and a zeta potential of −0.40±0.11 mV. After $^{64}$Cu—AuNC injection, mice were returned to enclosures while recovering from anesthesia.

Example 2: PCI Data Acquisition and Processing

To validate the method of passive cavitation imaging (PCI) on mouse brains, the following experiments were conducted.

The ultrasound image-guided focused ultrasound (FUS) system described in Ex. 1 was used to conduct PCI on the mice during administration of the FUS-BBBD treatment described in Ex. 1. The ultrasound imaging component was programmed to first operate in a pulse-echo mode to acquire a B-mode image for identifying the location of the mouse skull during PCI post-processing. The ultrasound imaging component was then operated in a passive mode for acquiring two sets of PCI data. The first PCI data acquisition was performed with FUS sonication on but before injection of microbubbles as described in Ex. 1 to define the background cavitation noise level. The second PCI data acquisition was performed immediately after microbubble injection and concurrently with the FUS sonication. During the sonication by each FUS pulse, one PCI frame was acquired with an acquisition duration of 400 µs.

A previously published frequency-domain PCI algorithm was implemented using Matlab (Mathworks Inc., Natick, Mass., USA) and used to process the PCI data offline. Parallel computation using Graphics Processing Units (GPUs) was integrated into the Matlab code to accelerate calculation speed. The algorithm applied a Butterworth bandpass filtering around the imaging probe bandwidth of 5-17 MHz to reduce contributions from FUS source signals. A phase shift in the frequency domain (equivalent to a time delay in temporal domain) was applied to the filtered PCI data acquired on each receiving element based on the propagation times between the receiving element and the spatial location that each pixel represented. The phase-shifted waveforms were summed across all receiving elements for each pixel. Waveform energy was computed by calculating the square of the summed waveforms. The mean amplitude of the spectrum was calculated within selected harmonic bandwidths (0.3 MHz window around all harmonics and superharmonics) for each pixel to generate stable cavitation (SC) maps. The mean amplitudes of broadband signals falling within frequency bands between the harmonic and ultraharmonic bands were used to calculate the inertial cavitation (IC) levels and to generate IC maps. The SC and IC maps obtained from each FUS treatment were integrated over time to obtain the stable cavitation dose (SCD) and inertial cavitation dose (ICD) maps, respectively.

Figure 2A:
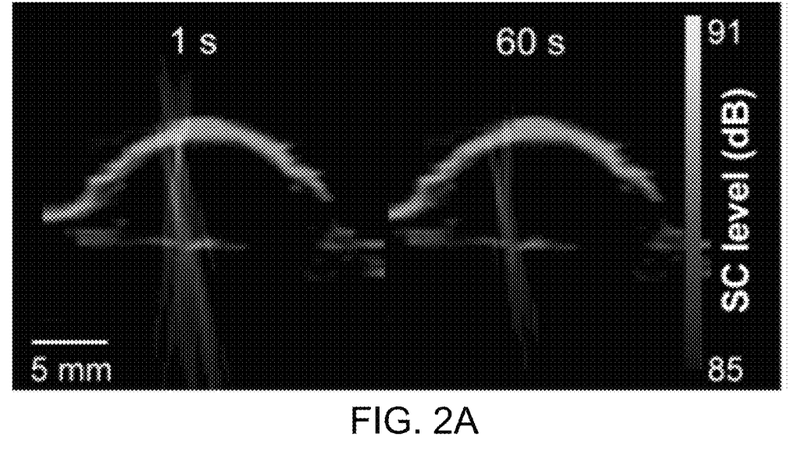
FIG. 2A contains representative SC level maps obtained during FUS treatment at two different time points (1 s and 60 s).
Figure 2B:
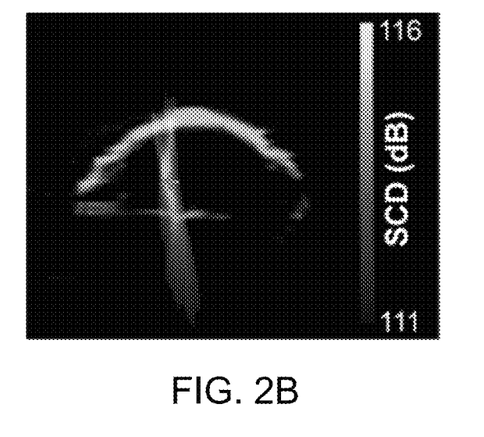
FIG. 2B is a representative SCD map acquired by integrating SC level maps similar to those of FIG. 2A through the total FUS treatment time for each pixel.
Figure 2C:
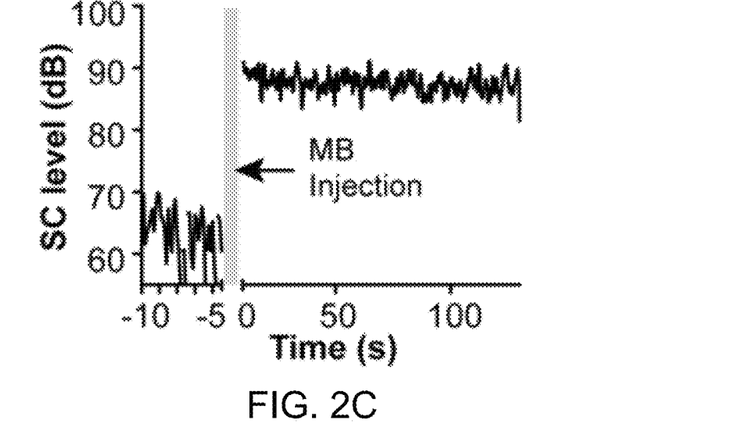
FIG. 2C is a representative SC level time curve for the pixel identified by the cross superimposed on the SCD map of FIG. 2B.
Figure 2D:
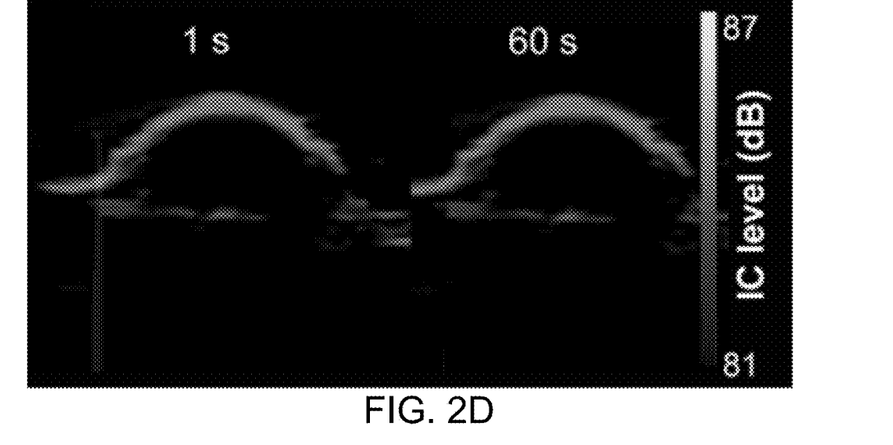
FIG. 2D contains representative IC level maps obtained during FUS treatment at two different time points (1 s and 60 s).
Figure 2E:
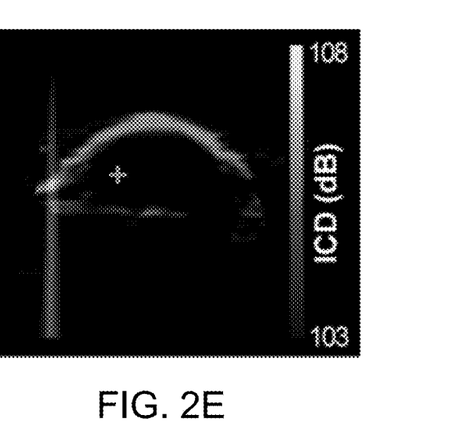
FIG. 2E is a representative ICD map acquired by integrating IC level maps similar to those of FIG. 2D through the total FUS treatment time for each pixel.
Figure 2F:
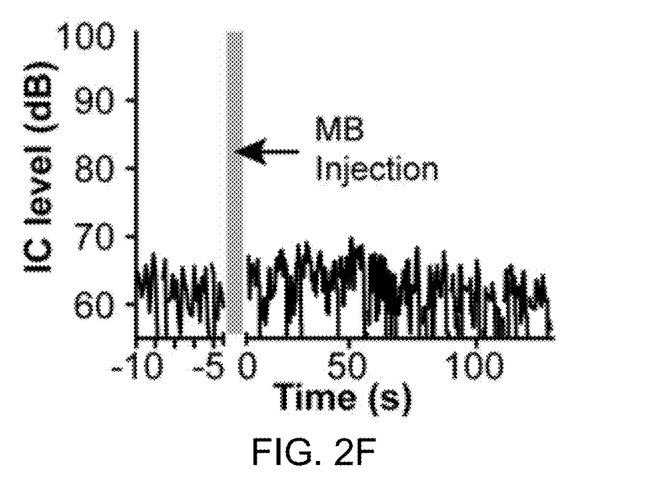
FIG. 2F is a representative IC level-time curve for the pixel identified by the cross superimposed on the ICD map of FIG. 2E.

PCI successfully recorded the spatiotemporal dynamics of microbubble cavitation activity in the mouse brain during the FUS treatment. FIG. 2A includes representative SC level maps (used to quantify the stable cavitation activity at individual time points) acquired at different time points (1 s and 60 s) during the FUS treatment. PCI also recorded the spatial distribution of the cavitation activity over time. FIG. 2B includes the SCD map generated by integrating the SC levels of FIG. 2A over the whole FUS treatment duration for each pixel to quantify total cavitation energy at each pixel. FIG. 2C summarizes the SC levels over time at one representative pixel (indicated by the superimposed cross of FIG. 2B). As illustrated in FIG. 2C, the SC level increased immediately after bolus injection of the microbubbles and then gradually decreased over the remaining time. FIGS. 2D, 2E, and 2F present the corresponding IC level map (FIG. 2D), IC dose (ICD) map (FIG. 2E), and IC level-time curve (FIG. 2F), which all indicated that the microbubble IC activity was at the noise level.

The results of this experiment demonstrated the feasibility of passive cavitation imaging (PCI) to assess the temporal dynamics of microbubble cavitation activity in mouse brains.

Example 3: In Vivo MicroPET/CT Image Acquisition and Processing

To assess the effect of FUS-BBBD treatment on the uptake of a therapeutic agent into a FUS-BBBD-treated brain region of a mouse, the following experiments were conducted.

Mice subjected to FUS-BBBD administration of the radiolabeled gold nanoclusters ($^{64}$Cu—AuNCs) as described in Ex. 1 were subjected to PET imaging 24 hrs. after the FUS-treatment to reduce interference of $^{64}$Cu—AuNCs circulating in blood vessels. PET images of the mice brains were acquired using an Inveon PET/CT system (Siemens, Knoxville, Tenn.).

The acquired PET images were co-registered with CT images after correcting for attenuation, scatter, normalization, and camera dead time. The PET images were reconstructed with the maximum a posteriori (MAP) algorithm to produce images with a pixel size of 0.8 mm and a spatial resolution of approximately 1.4 mm. Images were analyzed using Inveon Research Workplace (Siemens, Knoxville, Tenn.) and the Matlab program. Partial volume correction was performed following an established method to eliminate the spillover of signals from tissue outside the brain. Decay correction was applied to compensate for the decay of $^{64}$Cu over time. The pixel intensity of the PET image was quantified as percent injected dose per gram tissue (% ID/g).

Figure 3:
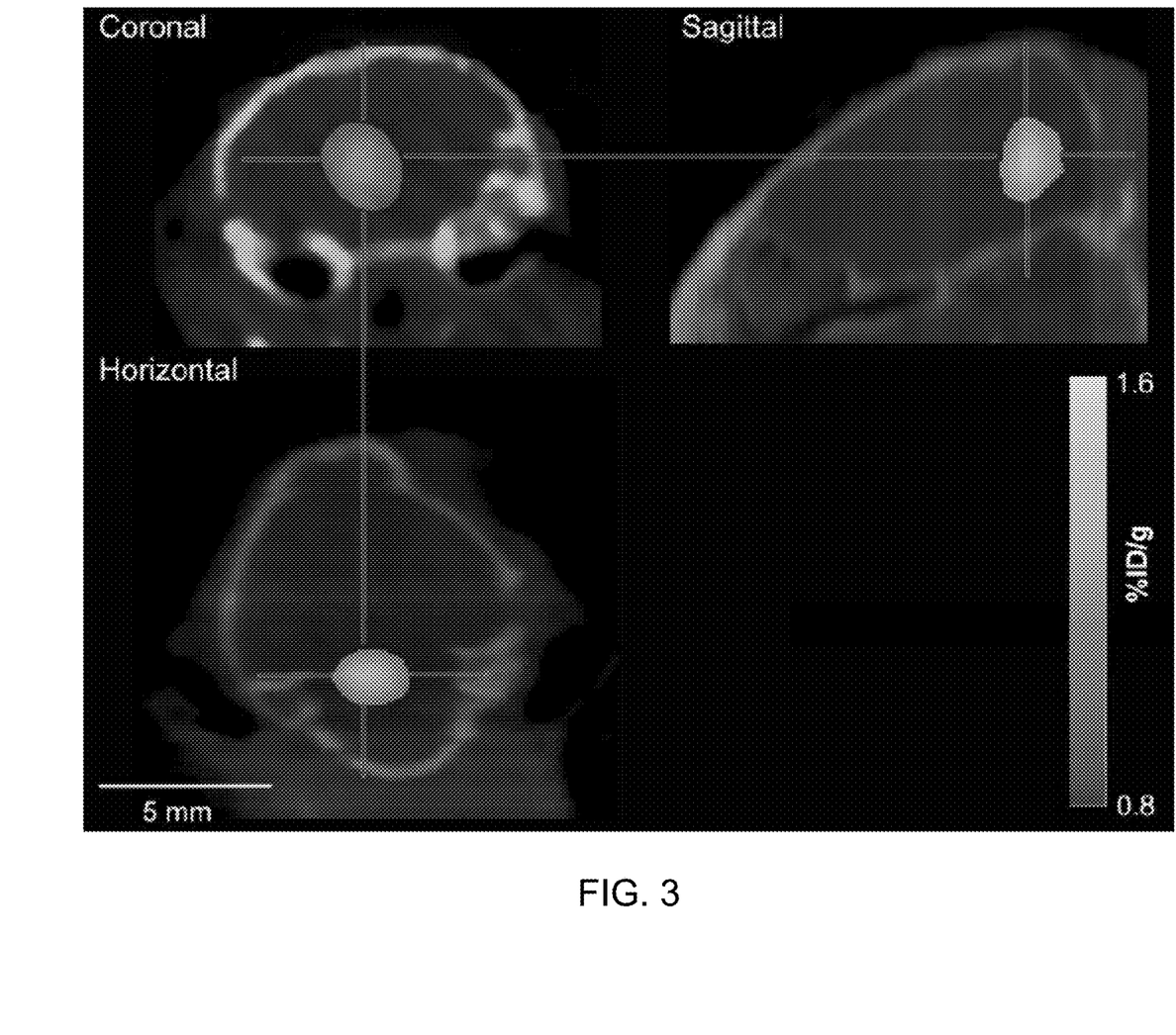
FIG. 3 contains representative PET images of a mouse in the coronal, sagittal, and horizontal planes.

Representative PET images are provided as FIG. 3. The concentrations of $^{64}$Cu—AuNCs delivered by FUS-BBBD was quantified in terms of percent injected dose per gram of tissue (% ID/g) and displayed as color maps superimposed on the PET images of FIG. 3. The color maps of FIG. 3 indicated successful delivery of $^{64}$Cu—AuNCs at the FUS-treated brain region of the mice, as indicated by higher radioactivity at the FUS-treated brain location compared with surrounding untreated brain regions.

The results of this experiment demonstrated that the uptake of $^{64}$Cu—AuNCs into the brains of mice was significantly enhanced by FUS-BBBD treatment relative to untreated brain regions.

Example 4: Correlation of PCI and PET Imaging

To validate the relationship of PCI-based quantification of cavitation stable cavitation dose (SCD) distribution as described in Ex. 2 to PET-based quantification of therapeutic compound uptake effectuated by FUS-BBBD treatment as described in Ex. 3, the following experiments were conducted.

Figure 1B:
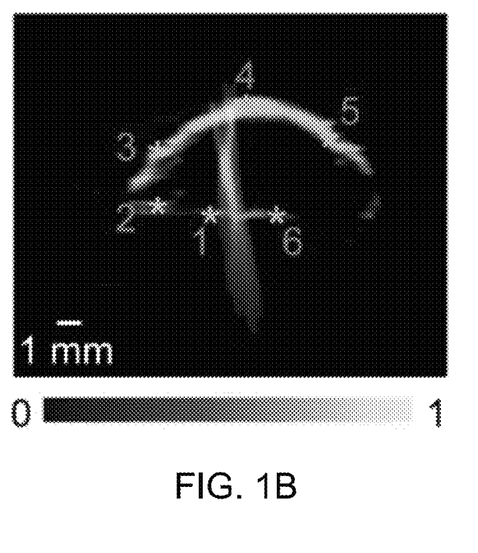
FIG. 1B is a representative PCI image acquired during a FUS treatment using the FUS-treatment system illustrated in FIG. 1A.
Figure 1C:
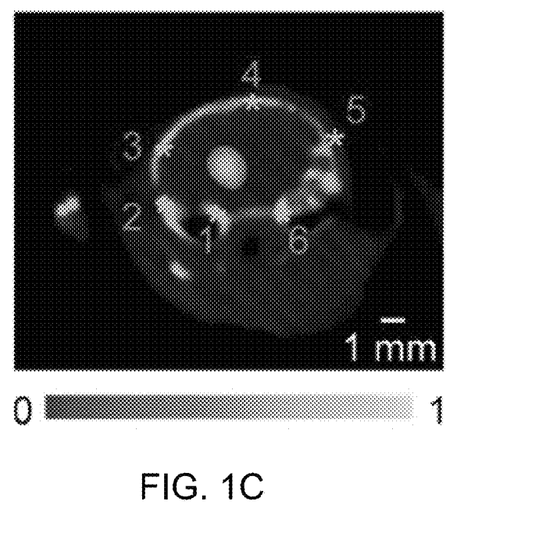
FIG. 1C is a representative PET/CT image acquired 24 h after a FUS treatment, corresponding to the PCI image of FIG. 1B.
Figure 1D:
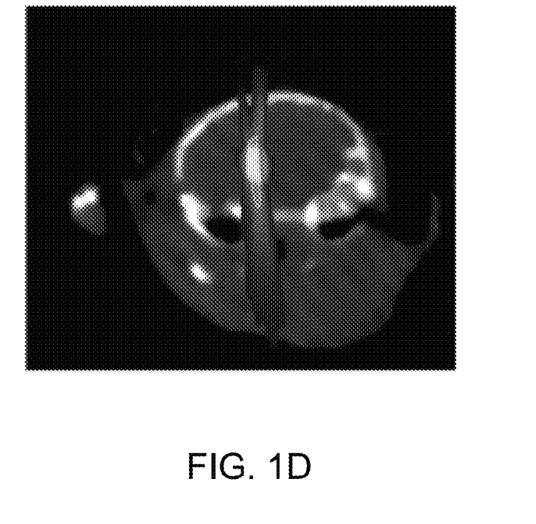
FIG. 1D is registration image between the PCI image of FIG. 1B and the PET/CT image of FIG. 1C, based on shared anatomic features of the skull as denoted by numbered asterisks) in both the PCT and PET/CT images.

As described in Ex. 1, the ultrasound imaging probe was co-axially aligned with the FUS transducer to position the focal point of the FUS transducer within the ultrasound imaging plane. PET images acquired as described in Ex. 3 were analyzed to identify the PET voxel location with the highest radioactivity inside the brain. This PET voxel location was assumed to be the location of the FUS focus during the FUS-BBBD treatment described in Ex. 1. PET images acquired in the coronal plane passing through this voxel were selected and assumed to correspond to the imaging plane for the B-mode/PCI images obtained as described in Ex. 2. The alignment of the selected PET imaging planes were confirmed by matching anatomic features of the mouse skulls in the B-mode images (see FIG. 1B) and in the corresponding CT images (see FIG. 1C). Six controlling points were selected on the B-mode and corresponding CT images, as denoted by numbers points superimposed on FIG. 1B an FIG. 1C, respectively. The CT images were translated and rotated to fit the corresponding controlling points on the B-mode images. Through this process, a transformation matrix was acquired and applied to the entire PET image to register the PET images with the corresponding PCI images for each mouse.

Figure 5A:
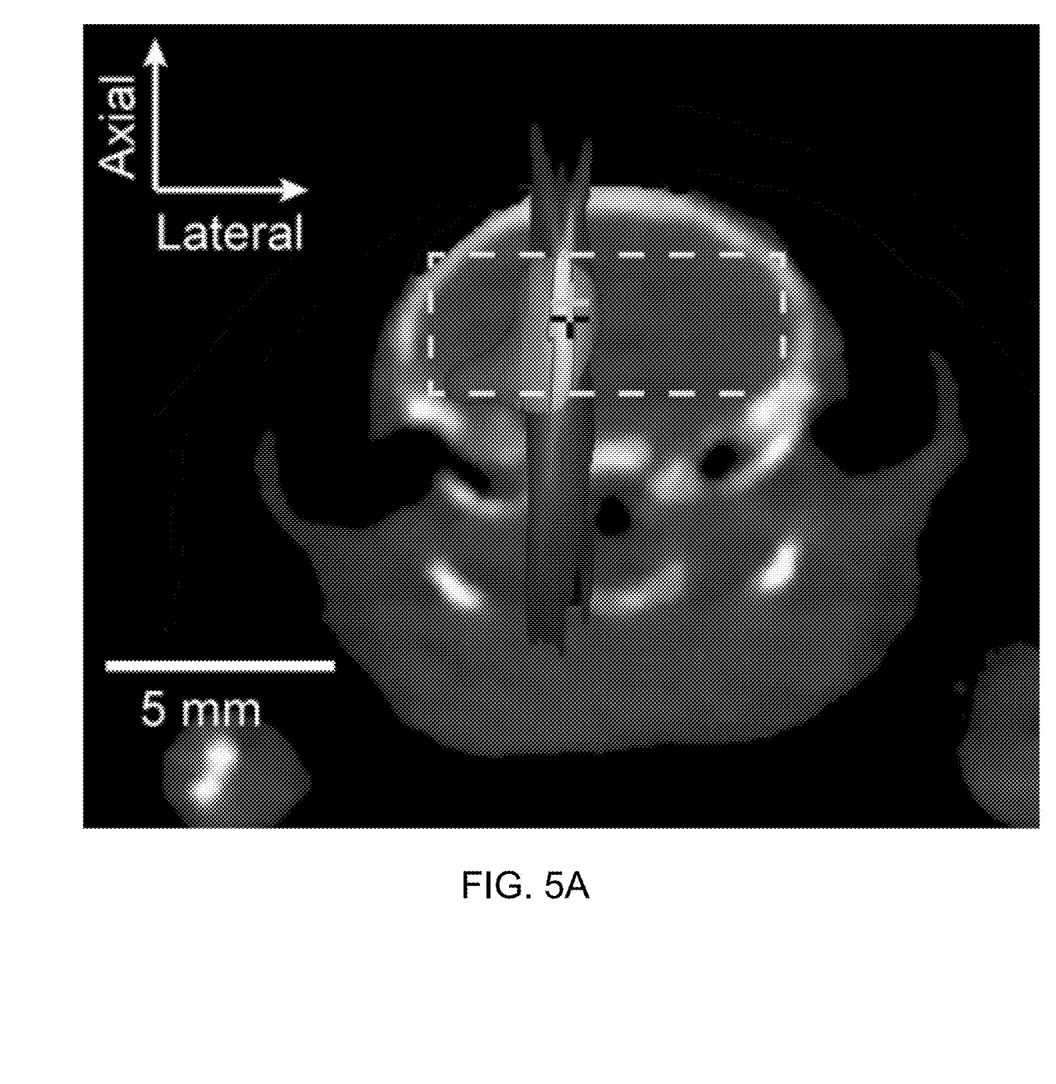
FIG. 5A is a representative SCD/$^{64}$Cu—AuNC concentration map with pixels corresponding to maximum SCD and maximum $^{64}$Cu—AuNC concentration indicated by superimposed crosses.

The capability of SCD in predicting $^{64}$Cu—AuNC delivery location was characterized by quantifying the offsets between the pixel location of the $SCD_{max}$ and the location with the maximum $^{64}$Cu—AuNC concentration. The offsets of these two locations were decomposed into lateral and axial directional components. The capability of SCD in predicting $^{64}$Cu—AuNCs concentration was assessed by evaluating the pixel-by-pixel correlation between the SCD map and the $^{64}$Cu—AuNC concentration map. The pixel size of the PET scanner was 0.8 mm×0.8 mm, corresponding to the intrinsic sampling size of the scanner. The SCD maps had a pixel size of 0.2 mm×0.2 mm. To perform a pixel by pixel comparison between these two maps, we first aligned the two images by aligning the pixel location of $SCD_{max}$ and the pixel with the highest $^{64}$Cu—AuNC concentration. The pixel resolution of the SCD map was reduced by downsampling to match that of the $^{64}$Cu—AuNC concentration map. The correlations between these two maps within the 2D region (see FIG. 5A) were evaluated using segmented linear regression implemented using GraphPad (Version 6.04, La Jolla, Calif., USA), and the goodness of fit was evaluated using the correlation coefficient, $R^2$. The pixel-by-pixel correlations between the SCD maps and the $^{64}$Cu—AuNC concentration maps were evaluated within a region in the brain selected based on the pixel position associated with $SCD_{max}$. The width of the selected region was defined by a lateral line within the brain passing through $SCD_{max}$ and the height of this region was defined by −1 dB of the $SCD_{max}$ in the axial direction to ensure the selected region was positioned inside the brain.

Figure 4A:
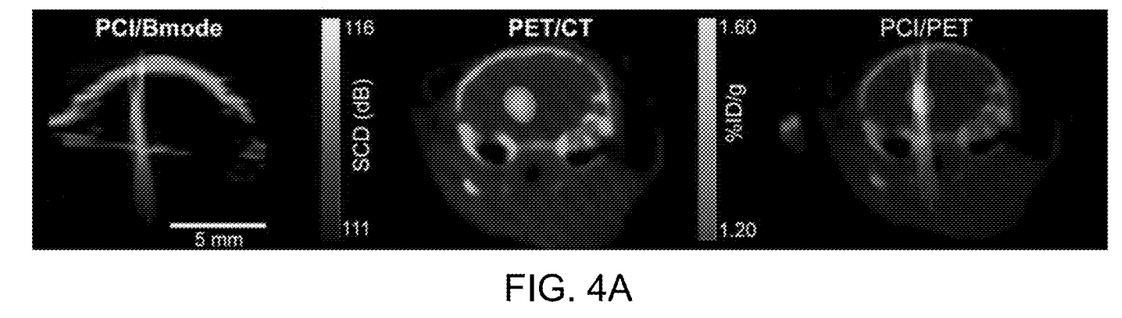
FIG. 4A contains representative PCI images (left column), PET images (middle column), and PCI/PET overlaid images (right column) for a first case.
Figure 4B:
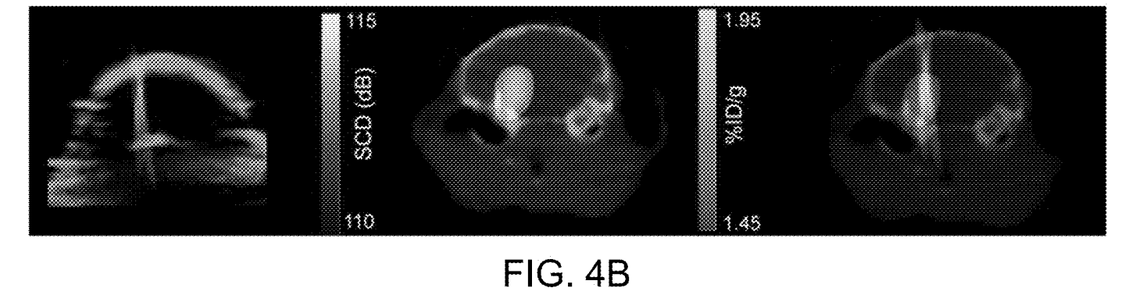
FIG. 4B contains representative PCI images (left column), PET images (middle column), and PCI/PET overlaid images (right column) for a second case.
Figure 4C:
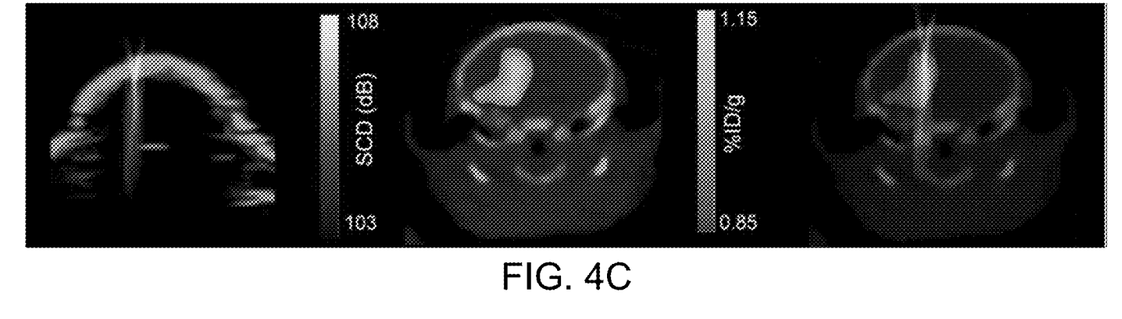
FIG. 4C contains representative PCI images (left column), PET images (middle column), and PCI/PET overlaid images (right column) for a third case.

FIGS. 4A, 4B, and 4C displays representative SCD maps (left column), $^{64}$Cu—AuNCs concentration maps acquired at approximately the same imaging plane as the SCD maps (center column), and overlay of these two maps (right column) for three representative cases. Although all mice demonstrated localized delivery of the $^{64}$Cu—AuNCs in the mouse brains after FUS-BBBD treatment using the same protocol, variations were detected between mice with respect to recorded microbubble cavitation activity and detected delivery concentrations of $^{64}$Cu—AuNCs. For the three cases illustrated in FIGS. 4A, 4B, and 4C, $SCD_{max}$ varied from 108 dB to 116 dB, and the maximum $^{64}$Cu—AuNCs concentrations varied within the range of 1.15-1.95% ID/g.

Figure 5B:
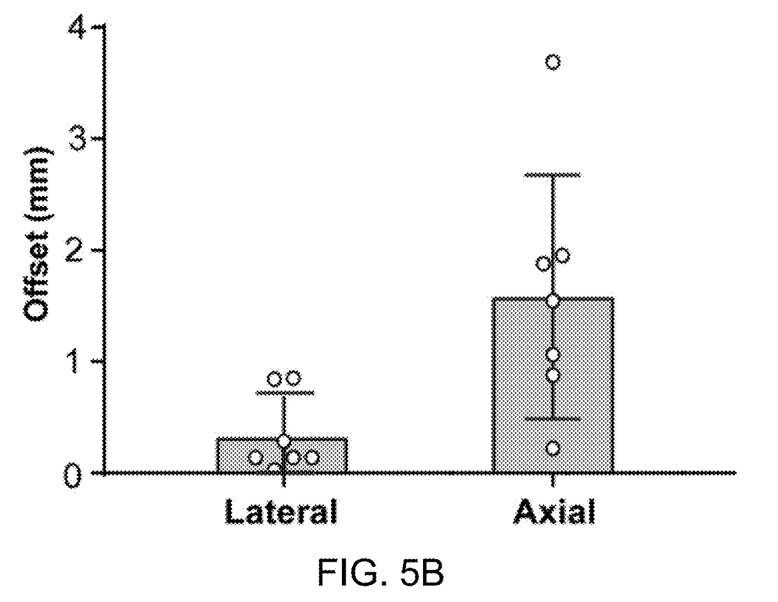
FIG. 5B is a graph summarizing lateral and axial offsets of the pixels corresponding to maximum SCDs and maximum $^{64}$Cu—AuNC concentrations within the brain as indicated by the superimposed crosses in FIG. 5A.
Figure 5C:
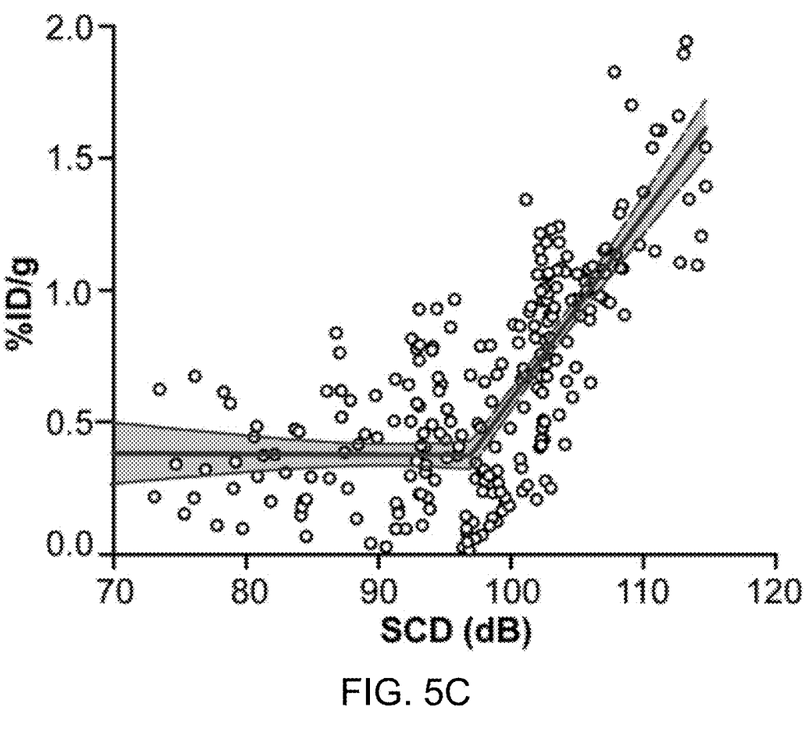
FIG. 5C is a graph summarizing a pixel-by-pixel correlation between SCD maps and $^{64}$Cu—AuNC concentration maps within the 2D region in the brain indicated by the superimposed rectangular box in FIG. 5A.

For all the treated mice, the offset between the pixel with maximum SCD ($SCD_{max}$) on the PCI maps and the pixel with the highest concentration of $^{64}$Cu—AuNCs on the PET images (see FIG. 5A) were 0.3±0.4 mm and 1.6±1.1 mm in the transverse and axial directions of the FUS beam, respectively, as summarized in FIG. 5B. As illustrated in FIG. 5C, a good linear correlation of $^{64}$Cu—AuNC concentration with respect to SCD was obtained within the selected brain region based on segmented linear regression ($R^2$=0.61). The segmented linear regression was used to model a threshold for BBBD in accordance with previously published methods.

The results of these experiments demonstrated a correlation between PCI-measured SCD values and delivery of $^{64}$Cu—AuNCs to brain tissue. Previously published results obtained a similar linear correlation based on an analysis of SCD quantified using PCD (1D) and the concentration of delivered agents quantified using ex vivo fluorescence imaging.

Example 5: Ex Vivo Quantification

Figure 6A:
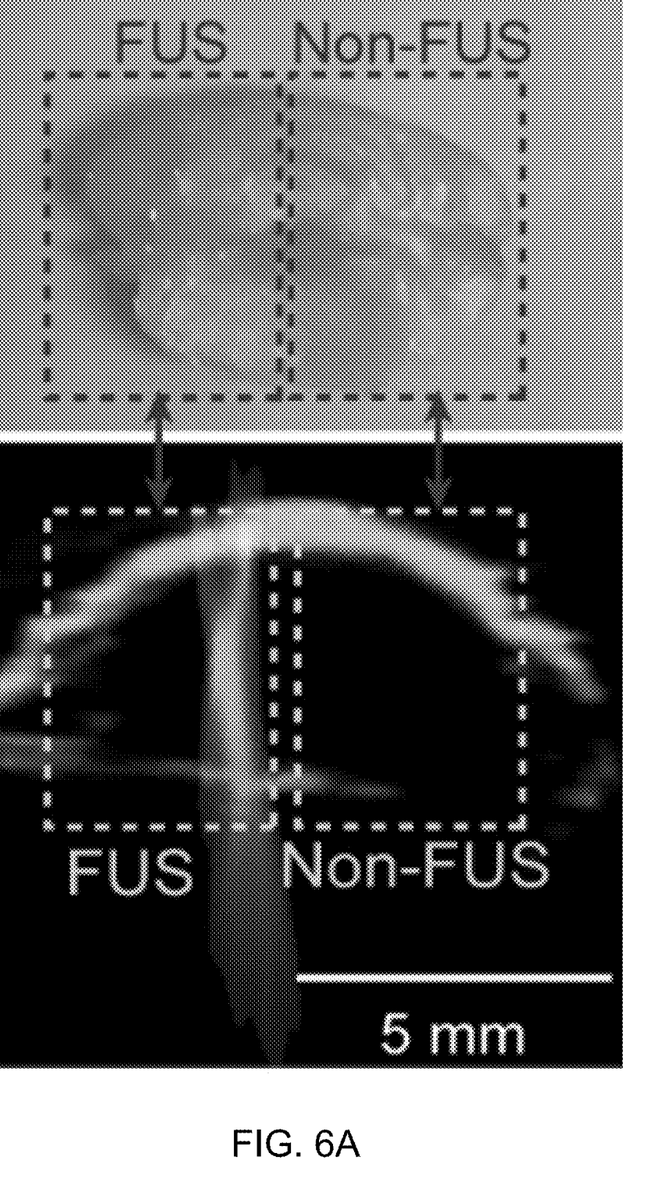
FIG. 6A contains photographic (upper) and PCI (lower) images of a coronal slice of a mouse brain containing brainstem targeted with $^{64}$Cu—AuNC with and without focused ultrasound-induced blood-brain barrier disruption (FUS), as indicated by superimposed rectangle boxes; SCD was averaged within each half of the brain for identifying a correlation between SCD and gamma counting.

To validate the correlation found between PCI and in vivo PET imaging as described in Ex. 4, nine additional mice were subjected to ex vivo quantification of $^{64}$Cu—AuNCs radioactivity using gamma counting and Au concentration of ICP-MS. Without being limited to any particular theory, previously published results demonstrated that the $^{64}$Cu radioactivity was linearly correlated with the measured Au concentration ($R^2$=0.94), indicating that the radioactivity of $^{64}$Cu can accurately measure the concentration of the AuNCs. The additional mice were treated using the FUS treatment protocol described in Ex. 1 to obtain PCI data and to administer $^{64}$Cu—AuNCs. After FUS treatment, the mice were sacrificed by transcardial perfusion 24 h after FUS treatment. The brains of the sacrificed mice were collected and sliced coronally into 2-mm slices. Those slices containing brainstem were separated into left and right halves, corresponding to FUS-treated and non-treated samples, respectively, as illustrated in FIG. 6A. The radioactivity of both halves were counted using a Beckman 8000 gamma counter (Beckman, Fullerton, Calif.). The count rate (counts per minute, CPM) for each tissue sample was corrected by automatic background subtraction. Decay correction was applied to compensate for the decay of $^{64}$Cu radioactivity over time. The corrected CPM from each tissue sample was normalized both to the mass of the tissue sample (in grams, g) and to the injected $^{64}$Cu—AuNCs dose (ID). The concentration of $^{64}$Cu—AuNCs in each tissue sample was then calculated as % ID/g. A correlation between the radioactivity (% ID/g) of $^{64}$Cu—AuNCs in the FUS-treated and contralateral non-treated brainstem samples and the corresponding spatial-averaged SCD values within the same regions was evaluated using the segmented linear regression method described in Ex. 4.

After completion of gamma counting, the brain stem samples were digested using a high-pressure microwave digestion system (Milestone Inc. Monroe, Conn.) and gold concentrations in the digested brain tissue samples were determined using ICP-MS (Elan DRC-e, PerkinElmer, Germany). Au standard was used to generate the standard curve. The concentration of delivered Au was expressed as the percentage of the Au in the brainstem over the total injected Au normalized by the tissue weight (% ID/g). Using the segmented linear regression used above, the measured Au concentration (% ID/g) in FUS-treated and non-treated brain stem tissue was correlated with the corresponding spatial-averaged SCD obtained as described above.

Figure 6B:
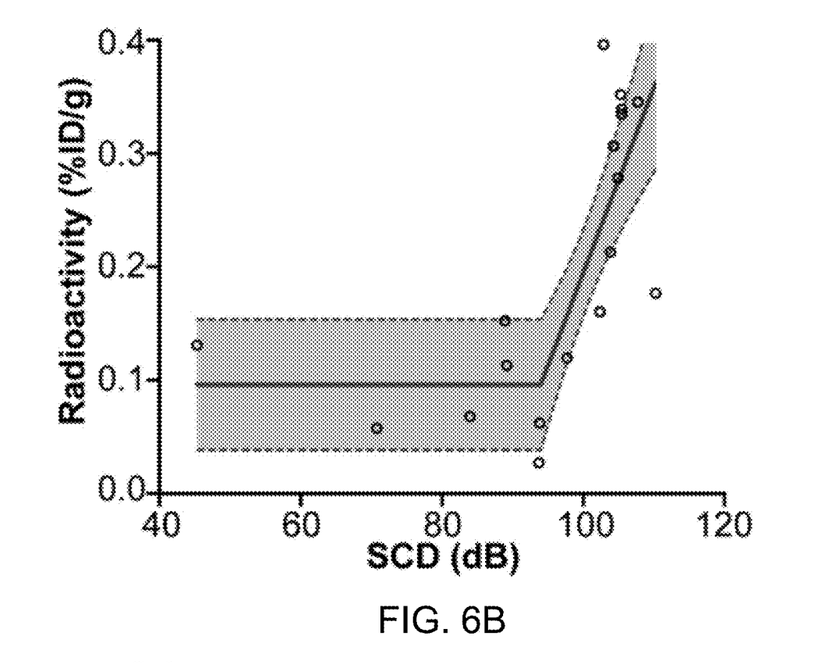
FIG. 6B is a graph summarizing radioactivity of $^{64}$Cu—AuNCs quantified using gamma counting in the FUS-treated halves and contralateral non-treated halves.
Figure 6C:
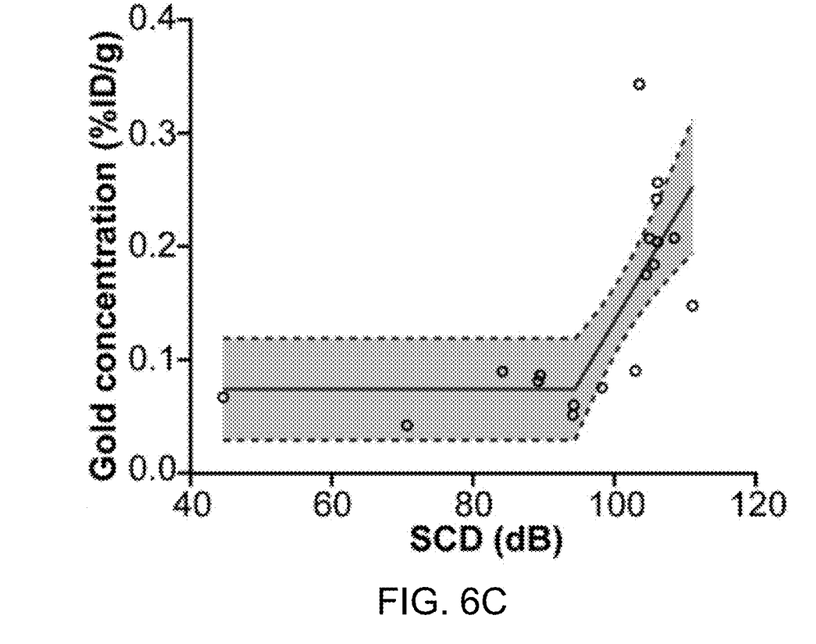
FIG. 6C is a graph summarizing gold concentration of $^{64}$Cu—AuNCs quantified using ICP-MS in the FUS-treated halves and contralateral non-treated halves.

$^{64}$Cu—AuNC concentrations quantified ex vivo in the FUS-treated halves and contralateral non-treated halves as described above were well correlated with the spatial-averaged SCD within the corresponding brain regions using the segmented linear regression, as illustrated in FIG. 6B (gamma counting, $R^2$=0.62) and FIG. 6C (ICP-MS, $R^2$=0.53). However, because the ex vivo study measured the average $^{64}$Cu—AuNC concentration in each half of the brain slices (see FIG. 6A), the measured concentrations (see FIGS. 6B and 6C) were lower than the corresponding concentrations obtained using PET (FIG. 5C).

The results of these experiments further demonstrated the correlation between PCI-measured SCD values and delivery of $^{64}$Cu—AuNCs to brain tissue.

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

What is claimed is:

1. A method of monitoring delivery of a therapeutic agent to a brain of a subject, the method comprising:
   treating the brain of the subject with a focused ultrasound in combination with microbubbles for blood-brain barrier disruption (FUS-BBBD);
   administering the therapeutic agent to the subject;
   obtaining a spatial map of a stable cavitation dose (SCD) using a passive cavitation imaging (PCI) system; and
   transforming the spatial map of the stable cavitation dose (SCD) to a map of a concentration of the therapeutic agent delivered to the brain of the subject using a pre-determined correlation of the stable cavitation dose (SCD) and the concentration of the therapeutic agent delivered to the brain of the subject, wherein the map of the concentration of the therapeutic agent is obtained in real time while modulating the treatment of the brain of the subject in real time.

2. The method of claim 1, further comprising obtaining the pre-determined correlation of the stable cavitation dose (SCD) and the concentration of the therapeutic agent delivered to the brain of the subject by:

treating at least one calibration subject with the focused ultrasound in combination with microbubbles for blood-brain barrier disruption (FUS-BBBD);

administering a radiolabeled therapeutic agent to the at least one calibration subject;

obtaining an SCD calibration map of the stable cavitation dose (SCD) for the at least one calibration subject using the passive cavitation imaging (PCI) system;

obtaining a delivered agent calibration map of a concentration of the radiolabeled therapeutic agent delivered to the brain for the at least one calibration subject using PET imaging; and correlating a plurality of the stable cavitation doses (SCD) at a plurality of locations within the SCD calibration map with a corresponding plurality of delivered agent concentrations at the plurality of locations within the delivered agent calibration map to obtain the pre-determined correlation.

3. The method of claim 2, wherein treating the brain of the subject with the focused ultrasound in combination with microbubbles for blood-brain barrier disruption (FUS-BBBD) further comprises spatially modulating an intensity of the focused ultrasound over the brain of the subject, wherein a spatial distribution of the concentration of the therapeutic agent varies in proportion to a spatial distribution of the intensity of the focused ultrasound over the brain of the subject.

4. The method of claim 3, further comprising spatially modulating the intensity of the focused ultrasound over the brain of the subject to match the map of the concentration of the therapeutic agent delivered to the brain of the subject to a desired distribution of the therapeutic agent.

5. The method of claim 1, further comprising controlling the operation of the passive cavitation imaging (PCI) system used to produce the focused ultrasound delivered to the brain of the subject in real time based on the map of the concentration of the therapeutic agent obtained in real time.

6. The method of claim 1, wherein the therapeutic agent is selected from the group consisting of a nanostructure, a chemotherapy drug, a peptide, a protein, and any combination thereof.

7. The method of claim 1, wherein administering the therapeutic agent to the subject further comprises administering the therapeutic agent by intravenous injection.

8. A method of delivering a desired spatial distribution of a therapeutic agent to a brain of a subject, the method comprising:

treating the brain of the subject with focused ultrasound in combination with microbubbles for blood-brain barrier disruption (FUS-BBBD);

administering the therapeutic agent to the subject;

obtaining a spatial map of stable cavitation dose (SCD) using a passive cavitation imaging (PCI) system;

transforming the spatial map of the stable cavitation dose (SCD) to a map of a concentration of the therapeutic agent delivered to the brain of the subject using a pre-determined correlation of the stable cavitation dose (SCD) and the concentration of the therapeutic agent delivered to the brain of the subject, wherein the map of the concentration of the therapeutic agent delivered to the brain of the subject is obtained in real time while treating the brain of the subject in real time with the focused ultrasound; and controlling the treatment of the subject with the focused ultrasound in real time to match the desired spatial distribution of the therapeutic agent to the map of the concentration of the therapeutic agent delivered to the brain of the subject.

9. The method of claim 8, further comprising obtaining the pre-determined correlation of the stable cavitation dose (SCD) and the concentration of the therapeutic agent delivered to the brain of the subject by:

treating at least one calibration subject with the focused ultrasound in combination with microbubbles for blood-brain barrier disruption (FUS-BBBD);

administering a radiolabeled therapeutic agent to the at least one calibration subject;

obtaining an SCD calibration map of the stable cavitation dose (SCD) for the at least one calibration subject using the passive cavitation imaging (PCI) system;

obtaining a delivered agent calibration map of a concentration of the radiolabeled therapeutic agent delivered to the brain for the at least one calibration subject using PET imaging; and correlating a plurality of the stable cavitation doses (SCD) at a plurality of locations within the SCD calibration map with a corresponding plurality of delivered agent concentrations at the plurality of locations within the delivered agent calibration map to obtain the pre-determined correlation.

10. The method of claim 8, further comprising controlling the operation of the passive cavitation imaging (PCI) system used to produce the focused ultrasound delivered to the brain of the subject in real time based on the map of the concentration of the therapeutic agent obtained in real time.

11. The method of claim 8, wherein the therapeutic agent is selected from the group consisting of a nanostructure, a chemotherapy drug, a peptide, a protein, and any combination thereof.

12. The method of claim 8, wherein administering the therapeutic agent to the subject further comprises administering the therapeutic agent by intravenous injection.

* * * * *